United States Patent [19]
Adams et al.

[11] 4,034,741
[45] July 12, 1977

[54] NOISE GENERATOR AND TRANSMITTER

[75] Inventors: Guy Emery Adams, Monroe; Jesse Carden, Jr., Piermont, both of N.Y.

[73] Assignee: Solitron Devices, Inc., Tappan, N.Y.

[21] Appl. No.: 658,596

[22] Filed: Feb. 17, 1976

[51] Int. Cl.$^2$ .................................... A61B 19/00
[52] U.S. Cl. .................. 128/1 C; 307/240; 331/78; 332/31 T
[58] Field of Search ............ 128/1 C, 1 R; 331/78, 331/38 M; 307/239, 240, 304; 332/31 T

[56] References Cited

U.S. PATENT DOCUMENTS

| | | | |
|---|---|---|---|
| 2,304,095 | 12/1941 | Hull | 128/1 C |
| 3,213,851 | 10/1965 | Currea | 128/1 R |
| 3,219,028 | 11/1965 | Giordano | 128/1 C |
| 3,404,235 | 10/1968 | Goldberg | 331/78 |
| 3,668,561 | 6/1972 | Krupa et al. | 332/31 T |
| 3,712,292 | 1/1973 | Zentmeyer, Jr. | 128/1 C |
| 3,718,987 | 3/1973 | Carver | 331/78 |
| 3,863,136 | 1/1975 | Hanson | 307/304 |

FOREIGN PATENT DOCUMENTS

| | | | |
|---|---|---|---|
| 1,165,541 | 10/1969 | United Kingdom | 128/1 C |

*Primary Examiner* — William E. Kamm
*Attorney, Agent, or Firm* — Richard G. Geib

[57] ABSTRACT

An analgesic noise generator employs a circuit that can be switched to provide a variable waveform from an active noise source out of an integrated circuit amplifier.

4 Claims, 3 Drawing Figures

NOISE GENERATOR AND TRANSMITTER

BACKGROUND

In todays active, mobilized society noise has become a common problem. No where is this felt more than when one is trying to fall asleep. In an effort to aid in sleeping the use of sleeping tablets has mushroomed. As is well known, however, this approach to the problem often creates physical and psychological side effects.

For this reason it was early on considered advantageous to induce sleep by physical methods. One such early method was to use electrodes to apply rectangular pulses. Another development was to create a hypnotic effect with lights, i.e., alternately dimming and brightening of a light source. Recently it has been recognized that white noise broadcast as a hum, for lack of a better worded description, can be quite effective as a sleep inducer. It is to the improvement of such an anlgesic nosie generator that this invention is directed. To that end the invention of patent application ser. No. 606,708 filed Aug. 21, 1975 now U.S. Pat. No. 3,993,043 assigned to the common assignee was conceived.

SUMMARY

This invention provides a device, for improving upon the aforesaid application in assisting the induction of natural sleep.

As stated above, this invention is concerned specifically with an improvement that will permit the creation of several waveforms such that an analgesic noise device can approximate soothing sounds of nature, i.e., waves, rain, wind.

A more detailed object of the invention is to provide a means in combination with a circuit of enhancement type MOS transistors controlling a noise source to circuits that will provide variable waveforms.

Still another object of this invention is to provide circuits as above that will provide waveforms of white noise that are variable from square waveform to saw tooth waveform to trangular waveforms and to steady waveforms.

DRAWING DESCRIPTION

DETAILED DESCRIPTION

Figure 1:
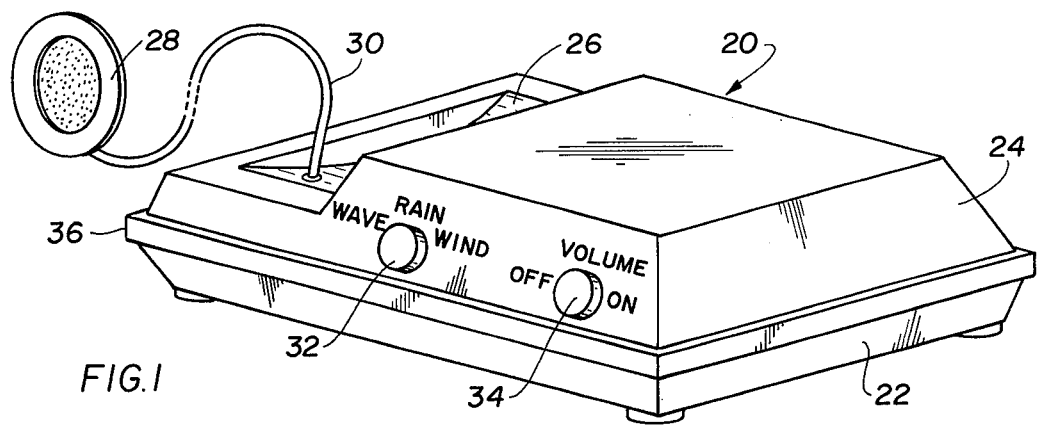
FIG. 1 is an isometric view of the portable sleep inducer unit constructed according to this invention.

With more particular reference now to FIG. 1 there is shown a housing 20 having a base 22 and a cover 24. The cover 24 has formed on one side a pocket 26 for stowage of a speaker 28 and a speaker cord 30. The cover also had, projecting from a front face, waveform control knob 32 and volume control 34. In the form shown the cover 24 is attached to the base 22 by a flange 36.

The base 22 as seen in the copending application has means for mounting batteries, and while two batteries are preferred there could be more used for additional fail-safe and lifetime provisioning. The batteries shown are of the usual nine volt variety common to transistor radios.

Also as seen in the copending application, the cover 24 provides the base for a printed circuit board bonded to the cover 24 with its discrete components projecting therefrom for easy service without removal of the board being necessary.

Figure 2:
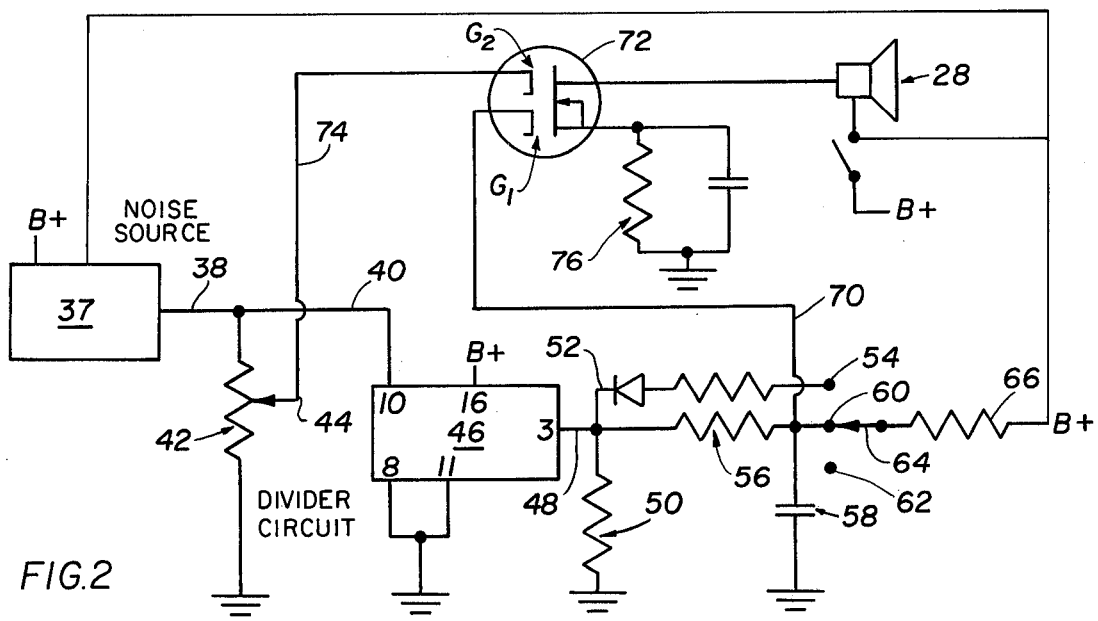
FIG. 2 is a circuit diagram of the interior circuit arrangement within the housing of FIG. 1.

With reference now to FIG. 2 there is shown the circuit which provides the improvement to the device shown by the copending application. More particularly, there is shown a noise source 37 connected by a lead 38 to a lead 40 to an IC chip, such as CD4020, at pin 10 thereof for input pulses. As may be readily appreciated by one skilled in the art of electronics the logic of an IC chip may be produced by discrete devices connected in a divider circuit. The particular chip chosen has a divide by 16,348 logic whereby at pin 3 one can get one pulse per second at pin 2 one half second and at pin one one quarter second. Variable resistance 42 with movable contact 44 is connected between lead 38 and a ground potential. Completing the connection of chip 46 is the connection of reset pin 11 and negative terminal 8 to a ground potential to permit continuous operation, the providing of a positive potential at pin 16 and an output lead 48 on pin 3 of chip 46 so as to provide one second pulses.

As can be seen a resistance 50 is connected between lead 48 and a ground potential at the point that a diode-resistance circuit 52 is connected thereto from a switching terminal 54 to which is also connected a resistor 56 between a capacitance 58 and switch terminal 60. Another switch terminal 62 is located with respect to switch 64 so as to controllably vary or preclude connection of resistance lead 66 from the B+ source to lead 48.

A lead 70 connects the output of resistance 56 to one of the gates of the insulated gate device 72 preferably $G_1$. The other gate ($G_2$) is connected by lead 74 to movable contact 44. Completing the circuit the speaker 28 is connected to the drain of the device 72 biased at its source in accordance with the resistance-capacitance circuit 76 connected to the ground potential. Device 72 is preferably a MOS FET as are commonly known in the market place.

OPERATION

In operation knob 34 is turned to close the switch and connect the positive potential B+ in the circuitry. At the same time knob 34 is turned to adjust slider 44 for the desired volume at speaker 28.

Noise source 37 as is familiar to one skilled in the art of manufacturing white (random) noise generators will then provide electrical noise to gate $G_2$ of device 72 at the intensity permitted by slider 44. This electrical noise also passes without regard to variable resistance 42 to provide input of electrical noise to chip 46 which will divide it down to provide a repetitive output from its buffered outputs such as the one per second pulse deliverable from pin 3 of the 4020 chip.

If knob 32 is in the wind position shown by FIG. 1, switch contact 64 is connecting resistance lead 66 to contact 62 whereby the lead 70 will deliver the output from divider chip 46 pin 3 to gradually increase the gain on gate $G_1$ of 72 and then with the same rate decrease the gain. This will produce electrical noise at the speaker 28 having a triangular waveform 78 of FIG. 3.

Figure 3:
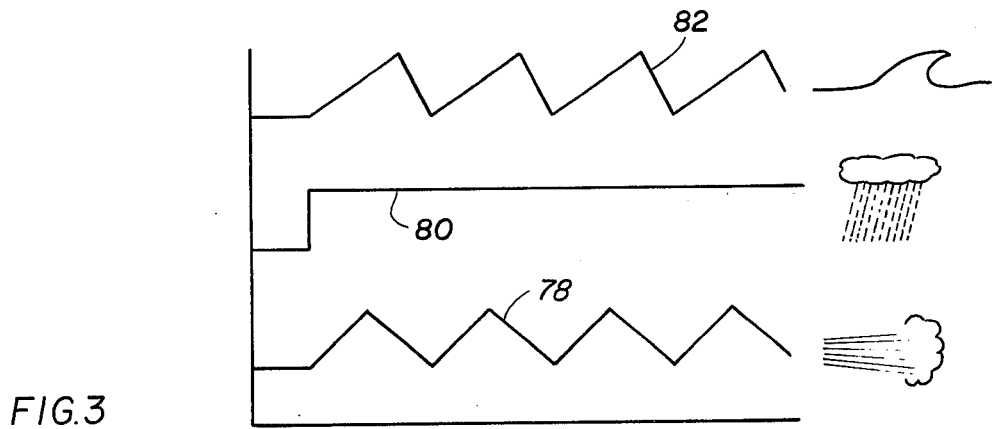
FIG. 3 is a graphical illustration of electrical noise waveforms possible with this invention.

If on the other hand switch arm 64 is as shown by FIG. 2 where the resistance lead 66 from B+ is connected directly to lead 70 to buck the output of chip 46 the gate $G_1$ is hard on and the electrical noise is steady from speaker 28, as shown by waveform 80 of FIG. 3.

In the other position of the arm 64, on contact 54, the positive potential is applied to the one per second output of chip 46 via resistance diode lead 52 so as to provide a gradual increase in gain at gate $G_1$ and a sharper decrease in the rate of fall of such gain. This will produce the more nearly sawtooth waveform 82 shown by FIG. 3.

As artistically represented adjacent thereto traces 78, 80 and 82 represent waveforms where the electrical noise will be representative of wind, rain and ocean waves.

In that numerous changes in structure may appear to one skilled in the art as such advances without departing from the scope of this invention, the above operative description is to be considered only in meeting with the statutory proscription of setting forth a preferred embodiment for this invention is that practitioners may realize how to build same once these Letters Patent are issued.

What is claimed is:

1. A random noise generator and transmitter comprising:
    a source of electrical energy;
    a switch for control of said source; source via
    a noise generating means connected to said source via said switch means to be productive of electrical noise;
    a means to broadcast electrical noise including a speaker and an insulated gate element connected to said speaker and to a resistance capacitance circuit in series with said insulated gate element and said speaker to said source via said switch, said insulated gate element having at least one gate connected to said noise generating means;
    a divide circuit connected to said noise generating means and said source of electrical energy; and
    a modulator circuit connected to said divide circuit and said source of electrical energy, said modulator circuit having an output terminal connected to another gate of said insulated gate element so as to control the desired waveform from said means.

2. A device for producing a soothing noise, said device including:
    first means to generate random noise;
    a variable volume control controlling level of random noise from said first means;
    second means connected to said first means to receive random noise therefrom, said second means being a divider circuit to divide said random noise into cycles of repetitive pusles; and
    third means to transmit said random noise in accordance with said pulses, said third means to transmit comprising a MOS FET element having one gate connected to the variable volume control connected to said first means and another gate to said second means whereby the repetitive pulses of said second means controls the transmission of the random noise from said first means by said third means.

3. The device of claim 2 and further characterized by a modulator circuit between said second and third means to provide an equal rate of gain increase and decrease, a steady gain and a first rate of increase and a different rate of decrease of the gain for said MOS FET.

4. A portable noise generator and transmitter comprising:
    a housing including a pocket;
    an electrical source within said housing;
    noise generating means in said housing;
    a divide circuit in said housing, said divide circuit connected to said noise generating means to divide same into repetitive pulses;
    insulated gate means in said housing having one gate connected to said noise generating means and another gate connected to said divide circuit;
    a modulator circuit between said divide circuit and said insulated gate means to provide an equal rate of gain increase, a steady gain and a first rate of increase and a different rate of decrease of the gain of the repetitive pulse of said divide circuit in obtaining the desired waveform from said insulated gate means of said noise generating means;
    a speaker to broadcast the product of said noise generating means via said insulated gate means, said speaker being stowable in the pocket of said housing; and
    control means on said housing to connect said electrical source to turn on and off said noise generating means said divide circuit and said modulator circuit and to control volume of said noise of said noise generating means.

* * * * *

UNITED STATES PATENT AND TRADEMARK OFFICE
CERTIFICATE OF CORRECTION

PATENT NO. : 4,034,741
DATED : July 12, 1977
INVENTOR(S) : Guy Emery Adams and Jesse Carden, Jr.

It is certified that error appears in the above-identified patent and that said Letters Patent are hereby corrected as shown below:

Column 3, Line 27, delete "source via" after the semicolon.

Column 4, Line 35, after "increase" and before the comma insert --- and decrease --- .

Signed and Sealed this

Fourth Day of October 1977

[SEAL]

Attest:

RUTH C. MASON
*Attesting Officer*

LUTRELLE F. PARKER
*Acting Commissioner of Patents and Trademarks*